United States Patent
Menon et al.

(10) Patent No.: US 9,265,440 B2
(45) Date of Patent: Feb. 23, 2016

(54) SPLIT BRIDGE FOR PET-MR SCANNER

(75) Inventors: Kanjimpuredathil Muralikrishna Menon, Bangalore (IN); Edward Emaci, Brookfield, WI (US); Jason Lee Philps, Hartland, WI (US); Shankar Murthy Udupa, Bangalore (IN); Rajeev Sahu, Bangalore (IN)

(73) Assignee: General Electric Company, Schenectady, NY (US)

( * ) Notice: Subject to any disclaimer, the term of this patent is extended or adjusted under 35 U.S.C. 154(b) by 564 days.

(21) Appl. No.: 13/483,112

(22) Filed: May 30, 2012

(65) Prior Publication Data

US 2013/0324835 A1 Dec. 5, 2013

(51) Int. Cl.
*A61B 5/055* (2006.01)
*G01R 33/48* (2006.01)
*A61B 5/00* (2006.01)
*A61B 6/03* (2006.01)
*A61B 6/04* (2006.01)
*A61B 6/00* (2006.01)

(52) U.S. Cl.
CPC .............. *A61B 5/055* (2013.01); *A61B 5/0035* (2013.01); *A61B 6/037* (2013.01); *A61B 6/0407* (2013.01); *A61B 6/4417* (2013.01); *G01R 33/481* (2013.01); *A61B 6/0442* (2013.01)

(58) Field of Classification Search
CPC ....... A61B 6/04; A61B 5/0555; A61B 6/4417
USPC .................................................. 600/407, 411
See application file for complete search history.

(56) References Cited

U.S. PATENT DOCUMENTS

| | | | |
|---|---|---|---|
| 7,218,112 B2 | 5/2007 | Ladebeck et al. | |
| 7,752,687 B1 * | 7/2010 | Denosky | 5/81.1 HS |
| 7,923,691 B2 | 4/2011 | Ladebeck | |
| 2003/0025582 A1 * | 2/2003 | Arz et al. | 335/296 |
| 2007/0039101 A1 * | 2/2007 | Luginbuhl et al. | 5/600 |
| 2008/0015430 A1 * | 1/2008 | Takamori | 600/415 |
| 2008/0039712 A1 | 2/2008 | Graves et al. | |
| 2008/0116351 A1 * | 5/2008 | Dave et al. | 248/646 |
| 2008/0312526 A1 | 12/2008 | Gagnon et al. | |
| 2009/0209844 A1 | 8/2009 | Gagnon et al. | |
| 2009/0260917 A1 * | 10/2009 | Maciejewski | 181/207 |
| 2009/0299170 A1 | 12/2009 | Gebhardt et al. | |
| 2010/0219347 A1 | 9/2010 | Schulz et al. | |
| 2011/0050226 A1 * | 3/2011 | Schellekens et al. | 324/309 |
| 2012/0018644 A1 * | 1/2012 | Caruba | 250/362 |

* cited by examiner

*Primary Examiner* — Rochelle Turchen
(74) *Attorney, Agent, or Firm* — Ziolkowski Patent Solutions Group, SC

(57) ABSTRACT

A PET-MRI apparatus includes a patient support assembly having a cradle to accommodate a subject, a carriage assembly to attach to the cradle and cause the cradle to selectively travel, and a rear bridge to receive the cradle and carriage. The patient support assembly also includes a front bridge to receive the cradle and carriage assembly and provide for translation therealong, with the front bridge including a first section and a second section that is spaced apart from the first section to form a gap in the front bridge between the first section and the second section in an area adjacent a PET detector array of the PET-MRI apparatus. The front and rear bridges include an anti-tip rail assembly to interact with the cradle and the carriage assembly so as to prevent tipping thereof when traversing over the gap between the first and second sections of the front bridge.

12 Claims, 6 Drawing Sheets

SPLIT BRIDGE FOR PET-MR SCANNER

BACKGROUND OF THE INVENTION

Embodiments of the invention relate generally to positron emission tomography (PET) and magnetic resonance (MR) imaging, and more specifically, to a combined PET-MR system incorporating a split bridge that provides patient support while reducing image degradation.

PET imaging involves the creation of tomographic images of positron emitting radionuclides in a subject of interest. A radionuclide-labeled agent is administered to a subject positioned within a detector ring. As the radionuclides decay, positively charged photons known as "positrons" are emitted therefrom. As these positrons travel through the tissues of the subject, they lose kinetic energy and ultimately collide with an electron, resulting in mutual annihilation. The positron annihilation results in a pair of oppositely-directed gamma rays being emitted at approximately 511 keV.

It is these gamma rays that are detected by the scintillators of the detector ring. When struck by a gamma ray, each scintillator illuminates, activating a photovoltaic component, such as a photodiode. The signals from the photovoltaics are processed as incidences of gamma rays. When two gamma rays strike oppositely positioned scintillators at approximately the same time, a coincidence is registered. Data sorting units process the coincidences to determine which are true coincidence events and sort out data representing deadtimes and single gamma ray detections. The coincidence events are binned and integrated to form frames of PET data which may be reconstructed into images depicting the distribution of the radionuclide-labeled agent and/or metabolites thereof in the subject.

MR imaging involves the use of magnetic fields and excitation pulses to detect the free induction decay of nuclei having net spins. When a substance such as human tissue is subjected to a uniform magnetic field (polarizing field $B_0$), the individual magnetic moments of the spins in the tissue attempt to align with this polarizing field, but process about it in random order at their characteristic Larmor frequency. If the substance, or tissue, is subjected to a magnetic field (excitation field $B_1$) which is in the x-y plane and which is near the Larmor frequency, the net aligned moment, or "longitudinal magnetization", $M_Z$, may be rotated, or "tipped", into the x-y plane to produce a net transverse magnetic moment $M_t$. A signal is emitted by the excited spins after the excitation signal $B_1$ is terminated and this signal may be received and processed to form an image.

When utilizing these signals to produce images, magnetic field gradients ($G_x$, $G_y$, and $G_z$) are employed. Typically, the region to be imaged is scanned by a sequence of measurement cycles in which these gradients vary according to the particular localization method being used. The resulting set of received NMR signals are digitized and processed to reconstruct the image using one of many well known reconstruction techniques.

In combination PET-MR systems, a patient handling system is required in order to carry the patient in and out of the bore of the imaging system. The patient handling system includes a bridge positioned within the bore that extends through a length of the imaging system, with the bridge providing a path and support for a patient support pallet or bed that translates therealong to move the patient through the imaging system. While in a standalone MR system, the structure and mass of the bridge within the bore has no effect on image acquisition and image quality, such is not the case in a PET-MR system. That is, unlike in a standalone MR system, a PET-MR system requires minimum mass in the region of the PET detector in order to provide for optimum image acquisition. Specifically, the mass in the PET detector region attenuates gamma rays, which reduces PET signal to the detectors and degrades image quality (IQ).

It would therefore be desirable to provide a bridge for use in a PET-MR system that helps in reducing the degradation of image quality. It would also be desirable for the bridge to provide improved image quality without compromising on patient support functionalities and serviceability.

BRIEF DESCRIPTION OF THE INVENTION

Embodiments of the invention provide a combined PET-MR system incorporating a split bridge that provides patient support while reducing image degradation.

In accordance with one aspect of the invention, a PET-MRI apparatus includes a magnetic resonance imaging (MRI) system having a plurality of gradient coils positioned about a bore of a magnet, and an RF coil assembly coupled to a pulse generator to emit an RF pulse sequence and arranged to receive resulting MR signals from a subject of interest in the bore, along with a positron emission tomography (PET) system having a detector array positioned around a PET tube encircling the bore, with the detector array being controlled to acquire PET emissions of the subject of interest. The PET-MRI apparatus also includes a patient support assembly configured to provide for support and movement of the subject of interest through the bore to enable acquisition of the MR signals and the PET emissions from the subject of interest, with the patient support assembly including a cradle configured to accommodate the subject of interest, a carriage assembly configured to attach to the cradle and cause the cradle to selectively travel through the bore, and a rear bridge configured to receive the cradle and carriage assembly and provide for translation therealong, the rear bridge extending outwardly from a back edge of the PET tube outside a volume of the bore. The patient support assembly also includes a front bridge configured to receive the cradle and carriage assembly and provide for translation therealong, with the front bridge being mounted to the PET tube and further including a first section extending from a front edge of the PET tube into the volume of the bore and a second section extending from the back edge of the PET tube into the volume of the bore, wherein the second section is spaced apart from the first section so as to form a gap in the front bridge between the first section and the second section in an area adjacent the detector array of the PET system, and wherein the rear bridge and front bridge include an anti-tip rail assembly configured to interact with the cradle and the carriage assembly so as to prevent tipping thereof when traversing over the gap between the first and second sections of the front bridge.

In accordance with another aspect of the invention, a patient support assembly for use in a combination PET-MRI imaging system includes a cradle configured to accommodate a subject of interest, a low profile carriage assembly (LPCA) attachable to the cradle and configured to drive the cradle through an imaging volume of the PET-MRI imaging system, and a bridge assembly configured to accommodate the cradle and LPCA and provide for translation therealong. The bridge assembly includes a rear bridge and a front bridge comprising a first section and a second section, with the front bridge comprising a split bridge that includes a gap formed between the first section and the second section in an area adjacent a PET detector array of the PET-MRI imaging system. The bridge assembly also includes an anti-tip rail assembly configured to interact with the cradle and the LPCA so as to prevent tipping thereof when traversing over the gap between the first and second sections of the front bridge.

In accordance with yet another aspect of the invention, a PET-MRI apparatus includes a magnetic resonance imaging (MRI) system configured to acquire MR signals from a subject of interest, the MRI system having a plurality of gradient coils positioned about a bore of a magnet and an RF coil assembly coupled to a pulse generator to emit an RF pulse sequence. The PET-MRI apparatus also includes a positron emission tomography (PET) system integrated into the MRI system and having a PET detector positioned on a PET tube encircling the bore, with the PET detector being controlled to acquire PET emissions of the subject of interest. The PET-MRI apparatus further includes a patient support assembly configured to provide for support and movement of the subject of interest through the bore to enable acquisition of the MR signals and the PET emissions from the subject of interest, with the patient support assembly including a low profile carriage assembly (LPCA) configured to drive a patient cradle so as provide for translation of the subject of interest through the bore, with the LPCA including a pair of slide blades formed thereon. The patient support assembly also includes a bridge assembly configured to provide for translation of the LPCA and cradle therealong, with the bridge assembly including a split front bridge having a gap formed therein in an area adjacent the detector array and with the split front bridge further including an anti-tip rail assembly configured to interact with the slide blades on the LPCA to prevent tipping of the LPCA when traversing over the gap in the split front bridge.

Various other features and advantages will be made apparent from the following detailed description and the drawings.

BRIEF DESCRIPTION OF THE DRAWINGS

The drawings illustrate embodiments presently contemplated for carrying out the invention.

In the drawings.

DETAILED DESCRIPTION

A patient support assembly for use in a PET-MR system is provided. The patient support assembly includes a split bridge having a gap therein that helps in reducing the degradation of PET image quality by minimizing mass in the region of the PET detector array. An anti-tip feature is integrated into the split bridge design that provides for gap crossover support of a low profile carriage assembly (LPCA) and cradle in the area of the PET detector array.

Figure 1:
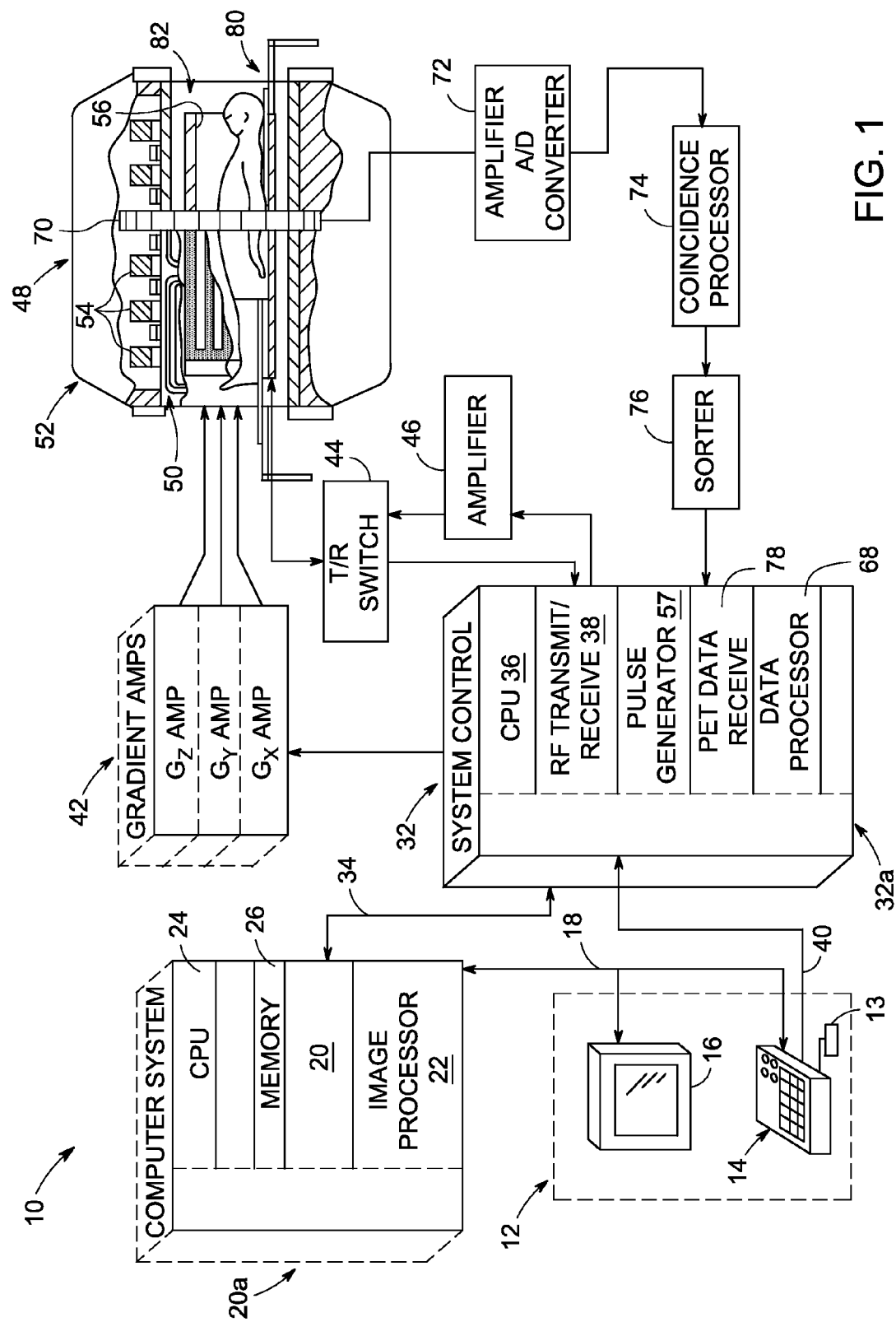
FIG. 1 is a schematic block diagram of an exemplary PET-MR imaging system for use with an embodiment of the invention.

Referring to FIG. 1, the major components of an exemplary hybrid PET-MR imaging system 10 that may incorporate embodiments of the present invention are shown. The operation of the system may be controlled from an operator console 12 which includes a keyboard or other input device 13, a control panel 14, and a display screen 16. The console 12 communicates through a link 18 with a separate computer system 20 that enables an operator to control the production and display of images on the display screen 16. The computer system 20 includes a number of modules, such as an image processor module 22, a CPU module 24 and a memory module 26. The computer system 20 may also be connected to permanent or back-up memory storage, a network, or may communicate with a separate system control 32 through link 34. The input device 13 can include a mouse, keyboard, track ball, touch activated screen, light wand, or any similar or equivalent input device, and may be used for interactive geometry prescription.

The system control 32 includes a set of modules in communication with one another and connected to the operator console 12 through link 40. It is through link 34 that the system control 32 receives commands to indicate the scan sequence or sequences that are to be performed. For MR data acquisition, an RF transmit/receive module 38 commands the scanner 48 to carry out the desired scan sequence, by sending instructions, commands, and/or requests describing the timing, strength and shape of the RF pulses and pulse sequences to be produced, to correspond to the timing and length of the data acquisition window. In this regard, a transmit/receive switch 44 controls the flow of data via amplifier 46 to scanner 48 from RF transmit module 38 and from scanner 48 to RF receive module 38. The system control 32 also connects to a set of gradient amplifiers 42, to indicate the timing and shape of the gradient pulses that are produced during the scan.

The gradient waveform instructions produced by system control 32 are sent to the gradient amplifier system 42 having Gx, Gy, and Gz amplifiers. Amplifiers 42 may be external of scanner 48 or system control 32, or may be integrated therein. Each gradient amplifier excites a corresponding physical gradient coil in a gradient coil assembly generally designated 50 to produce the magnetic field gradients used for spatially encoding acquired signals. The gradient coil assembly 50 forms part of a magnet assembly 52 which includes a polarizing magnet 54 and an RF coil assembly 56. Alternatively, the gradient coils of gradient coil assembly 50 may be independent of the magnet assembly 52. RF coil assembly may include a whole-body RF transmit coil 56 as shown. The coils 56 of the RF coil assembly may be configured for both transmitting and receiving, or for transmit-only or receive-only. A pulse generator 57 may be integrated into system control 32 as shown, or may be integrated into scanner equipment 48, to produce pulse sequences or pulse sequence signals for the gradient amplifiers 42 and/or the RF coil assembly 56. In addition, pulse generator 57 may generate PET data blanking signals synchronously with the production of the pulse sequences. These blanking signals may be generated on separate logic lines for subsequent data processing. The MR signals resulting from the excitation pulses, emitted by the excited nuclei in the patient, may be sensed by the whole body coil 56 and are then transmitted to the RF transmit/receive module 38 via T/R switch 44. The MR signals are demodulated, filtered, and digitized in the data processing section 68 of the system control 32.

An MR scan is complete when one or more sets of raw k-space data has been acquired in the data processor 68. This raw k-space data is reconstructed in data processor 68 which operates to transform the data (through Fourier or other techniques) into image data. This image data is conveyed through link 34 to the computer system 20 where it is stored in memory 26. Alternatively, in some systems computer system 20 may assume the image data reconstruction and other functions of data processor 68. In response to commands received from the operator console 12, the image data stored in memory 26 may be archived in long term storage or may be further processed by the image processor 22 or CPU 24 and conveyed to the operator console 12 and presented on the display 16.

In combined MR-PET scanning systems, PET data may be acquired simultaneously with the MR data acquisition described above. Thus, scanner 48 also contains a positron emission detector array or ring 70, configured to detect gamma rays from positron annihilations emitted from a subject. Detector array 70 preferably includes a plurality of scintillators and photovoltaics arranged about a gantry. Detector array 70 may, however, be of any suitable construction for acquiring PET data. In addition, the scintillator packs, photovoltaics, and other electronics of the detector array 70 need not be shielded from the magnetic fields and/or RF fields applied by the MR components 54, 56. However, it is contemplated that embodiments of the present invention may include such shielding as known in the art, or may be combined with various other shielding techniques.

Gamma ray incidences detected by detector array 70 are transformed, by the photovoltaics of the detector array 70, into electrical signals and are conditioned by a series of front-end electronics 72. These conditioning circuits 72 may include various amplifiers, filters, and analog-to-digital converters. The digital signals output by front end electronics 72 are then processed by a coincidence processor 74 to match gamma ray detections as potential coincidence events. When two gamma rays strike detectors approximately opposite one another, it is possible, absent the interactions of random noise and signal gamma ray detections, that a positron annihilation took place somewhere along the line between the detectors. Thus, the coincidences determined by coincidence processor 74 are sorted into true coincidence events and are ultimately integrated by data sorter 76. The coincidence event data, or PET data, from sorter 76 is received by the system control 32 at a PET data receive port 78 and stored in memory 26 for subsequent processing 68. PET images may then be reconstructed by image processor 22 and may be combined with MR images to produce hybrid structural and metabolic or functional images. Conditioning circuits 72, coincidence processor 74 and sorter 76 may each be external of scanner 48 or system control 32, or may be integrated therein.

As further shown in FIG. 1, a patient support assembly 80 is included in PET-MR imaging system 10 to support the patient within the imaging system during data acquisition. The patient support assembly 80 extends into a main magnet bore 82 of the imaging system 10 and extends through the imaging system so that its length is generally parallel to the bore axis. The patient support assembly 80 enables movement of the patient into various positions with respect to the imaging system 10, including a loading position outside the bore of imaging system 10 and at least one imaging position, where at least a portion of a patient is positioned within an imaging volume (i.e., within the bore) when at the imaging position.

Figure 2:
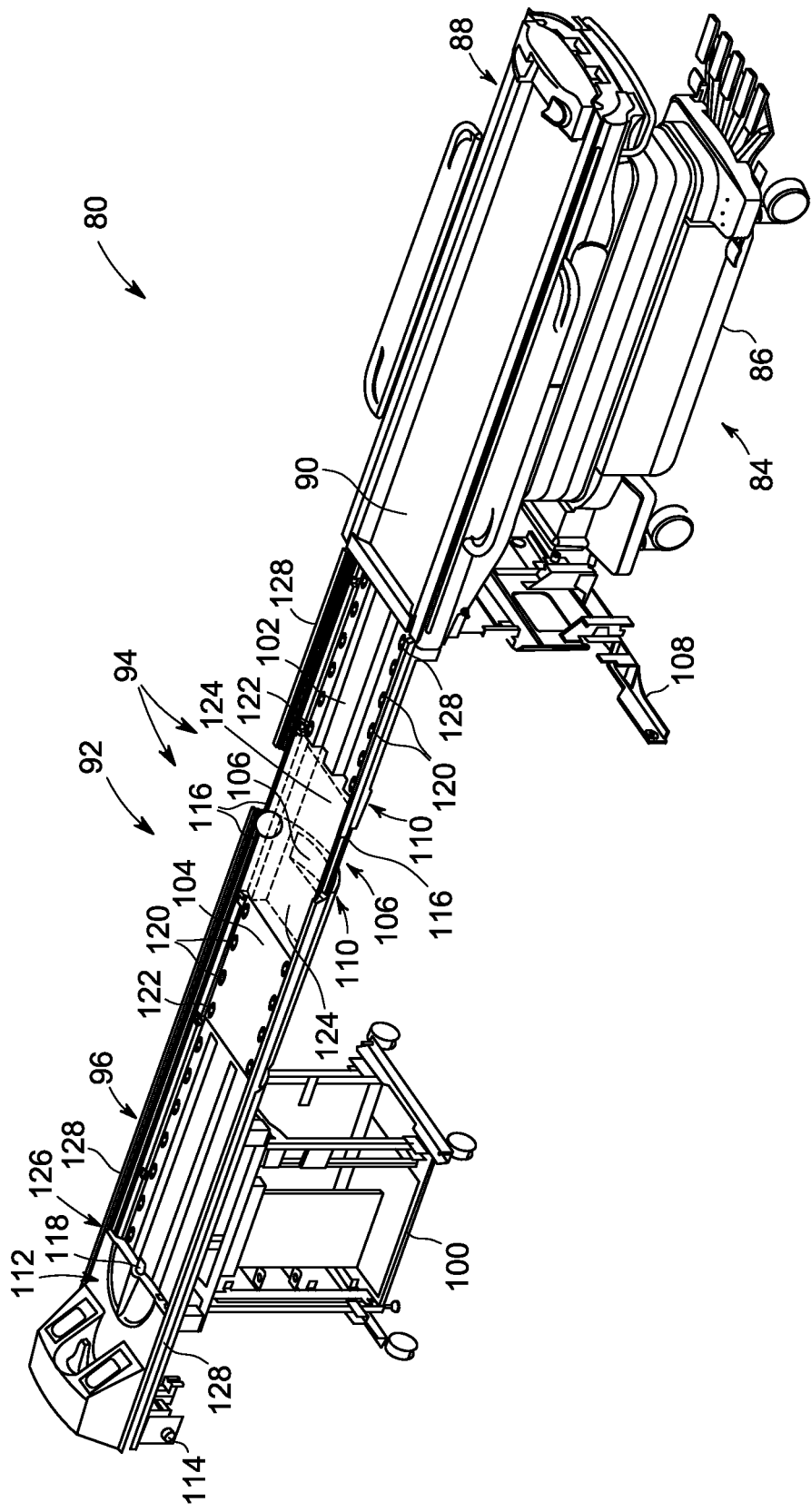
FIG. 2 is a perspective view of a patient support assembly according to an embodiment of the invention.
Figure 3:
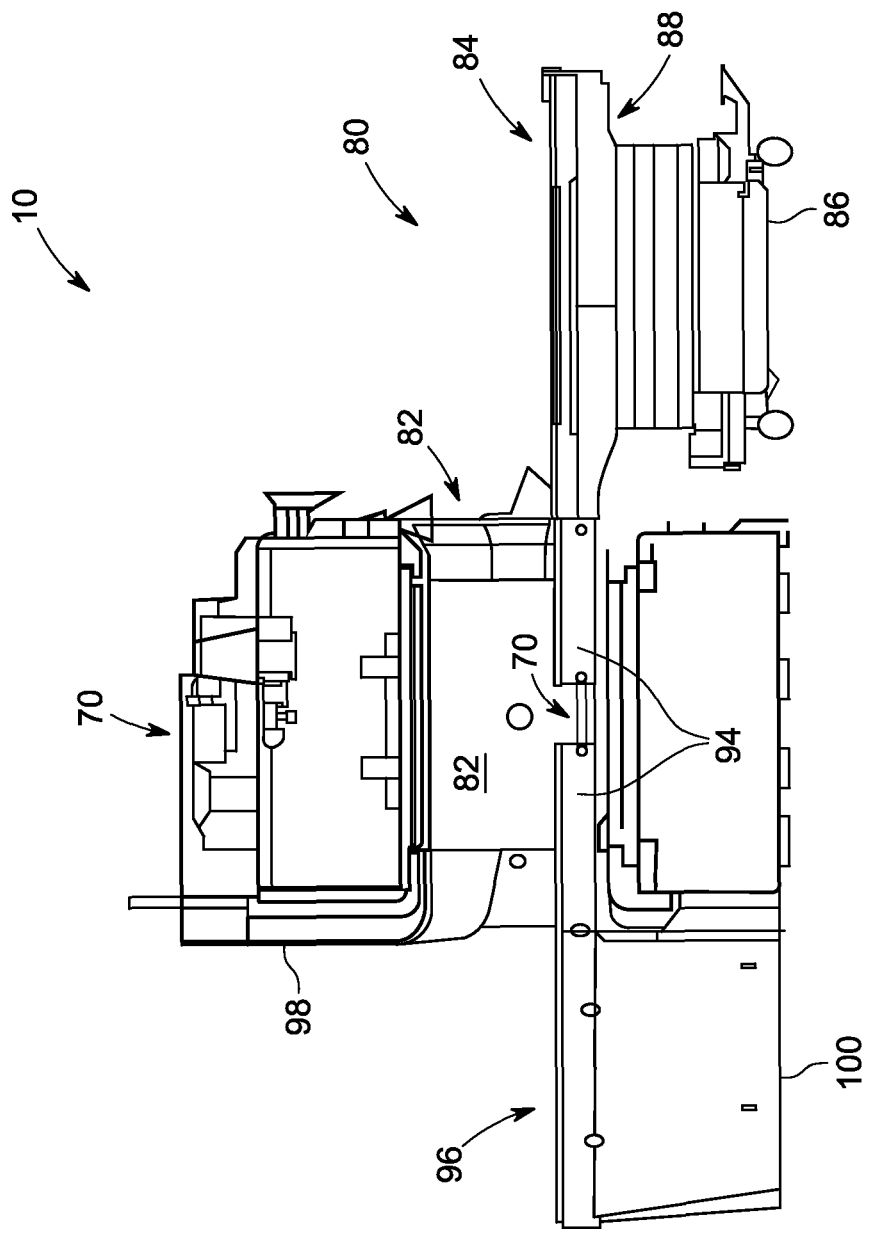
FIG. 3 is a side elevational view of the PET-MR imaging system of FIG. 1, incorporating the patient support assembly of FIG. 2, according to an embodiment of the invention.

Referring now to FIGS. 2 and 3, a detailed view of the patient support assembly 80 is shown. The patient support assembly 80 includes a patient bed 84 that supports the patient and provides for transport of the patient to and from the imaging system 10. The patient bed 84 includes a base structure 86 and a table 88 that is removable from the base structure 86 to enable transfer of the patient from the bed into the bore 82 of the PET-MR imaging system 10 for performing of an imaging scan. The table 88 further includes a cradle 90 that facilitates movement of the table through the imaging system 10. According to an exemplary embodiment, the cradle 90 is constructed as a thin, Kevlar cradle. The height of the patient bed 84 may be adjusted as needed in order to position the table 88 appropriately for transfer of the patient into the imaging system 10, such that the cradle 90 may slide off of the base structure 86 and into the imaging system 10.

Also included in patient support assembly 80 is a bridge assembly 92 having a front bridge 94 and a rear bridge 96. The bridge assembly 92 provides a path for the patient cradle 90 to move within and through the bore 82 of imaging system 10 (FIG. 1) to move the patient to desired imaging locations within the imaging system 10. According to an exemplary embodiment, the rear bridge 96 and front bridge 94 have a construction of a foam core with a skin of Kevlar or another fiber reinforced plastic (FRP), so as to provide a strong bridge with a minimal amount of material and thereby minimize PET attenuation resulting from the bridge.

As seen in FIG. 2, the rear bridge 96 extends outward from a rear edge 98 of imaging system 10, with the rear bridge 96 being supported by a rear pedestal structure 100. The front bridge 94 has a split bridge configuration and includes a first section 102 and a second section 104 that are separated from one another by a gap 106. An outer edge of first section 102 is supported by a front bridge mounting 108, with the front bridge mounting 108 providing adjustability regarding connection of the first section 102 thereto. An outer edge of second section 104 is assembled with and connected to rear pedestal structure 100 so as to be supported thereby. An inner edge 110 of each of the first and second sections 102, 104 is mounted directly to the imaging system 10 (i.e., to a PET tube of the imaging system) so as to be anchored thereto, as will be explained in greater detail below.

According to embodiments of the invention, the inner edge 110 of each of the first and second sections 102, 104 of front bridge 94 is located adjacent to either side of detector array 70 of imaging system 10 (FIG. 1), such that the detector array 70 is aligned with the gap 106 between the first and second sections 102, 104. Beneficially, the aligning of the detector array 70 and the gap 106 between the first and second sections 102, 104 of front bridge 94 minimizes mass in the region of the detector array 70, so as to thereby reduce the attenuation of gamma rays during PET imaging that may result from the presence of such mass. The PET signal received by the detectors in detector array 70 is thus improved and the degradation of the image quality (IQ) is minimized.

A low profile cradle assembly (LPCA) 112 is also included in patient support assembly 80 for purposes of enabling the translation of cradle 90 along bridge assembly 92. The LPCA 112 is driven by a dual drive 114 that includes a pair of drive belts 116 for propelling the LPCA 112 along a length of the bridge assembly 92, with the belts extending over gap 106, such that LPCA 112 and cradle 90 continue to be driven by dual drive even when traversing the gap 106. As shown in FIG. 2, the LPCA 112 may originally be positioned at a far end of rear bridge 96. When a patient is transported to PET-MR imaging system 10 via patient bed 84 for purposes of an imaging scan, the LPCA 112 is driven by dual drive 114 along rear bridge 96 and along front bridge 94 to be brought into proximity of patient bed 84. The LPCA 112 is brought into contact with cradle 90 of the patient table 88, such that a hook 118 or similar type latching mechanism is caused to engage a receptacle or receiving mechanism (not shown) on cradle 90. Upon securing of LPCA 112 to cradle 90, the LPCA 112 and cradle 90 may be translated along bridge assembly 92 as desired to position the patient in a plurality of imaging positions within bore 82 of imaging system 10.

As shown in FIG. 2, the rear bridge 96 and the front bridge 94 each include a plurality of vertically oriented roller bearings or wheels 120 spaced along a length of the front and rear bridges 94, 96 for supporting cradle 90 and LPCA 112 during translation thereof along the entire scan range, with pairs of spaced apart roller bearings 120 being positioned along a length of the front and rear bridges 94, 96. According to one embodiment of the invention, a number of horizontally oriented tapered wheels 122 (or similar guiding devices) is also included on rear bridge 96 and the front bridge 94 at select locations. The horizontally oriented tapered wheels 122 function to assist in laterally positioning cradle 90 and LPCA 112 on bridge assembly 92, such that the cradle 90 and LPCA 112 remain centered on the bridge assembly 92.

Referring still to FIG. 2, it is seen that each of the first and second sections 102, 104 of front bridge 94 includes a cut-out area or portion 124 therein in an area adjacent the inner edge 110 of the respective first and second sections 102, 104, next to gap 106. The cut-out areas 124 of the first and second sections 102, 104 of front bridge 94 collectively form an area for housing a coil matrix array (CMA) (not shown) of the PET-MR imaging system 10. To assist the LPCA 112 and cradle 90 in traversing over the cut-out areas 124 and across gap 106, vertically oriented roller bearings or wheels 120 are included on front bridge 94 in the cut-out areas 124 of the first section and second sections 102, 104. According to an exemplary embodiment, six roller bearings 120 are positioned in the cut-out areas 124 of first section and second sections 102, 104 at locations that correspond to open slots in the CMA. By positioning roller bearings 120 at locations that pass through open slots on the CMA, any load transfer from the bearings to the CMA is prevented.

As indicated above, the construction of front bridge 94 as a split bridge, having a first section 102 that is separated from a second section 104 by a gap 106, results in minimum mass in the region of the PET detector array 70, such that any unnecessary attenuation of gamma rays by the bridge assembly that might reduce the PET signal to the detector array 70 is minimized, and any degradation of image quality is prevented. However, it is recognized that the presence of gap 106 between the first and second sections 102, 104 of front bridge 94 can cause problems with regard to the LPCA 112 and cradle 90 traversing the front bridge 94. That is, since LPCA 112 is shorter in length, there is tendency for the LPCA 112 to tip and fall into gap 106 while crossing thereover. In order to prevent such tipping of the LPCA 112 and/or cradle 90 as it passes over gap 106, an anti-tip rail assembly 126 including anti-tip guide rails 128 are provided on front and rear bridges 94, 96 that interact with the LPCA 112 and cradle 90 to prevent tipping thereof. As shown in FIG. 2, the rails 128 on front bridge 94 extend from the first section 102 to the second section 104, so as to extend over gap 106.

Figure 4:
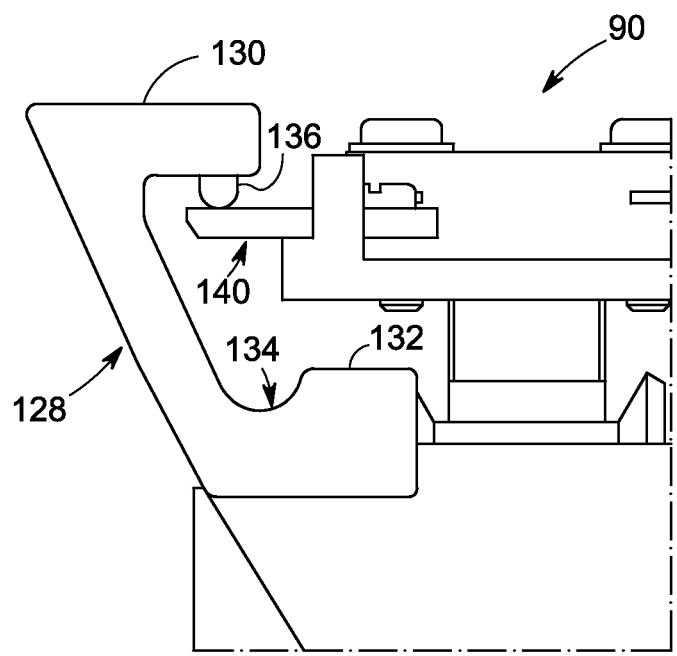
FIG. 4 is an end view of a portion of the patient support assembly of FIG. 2 according to an embodiment of the invention.
Figure 5:
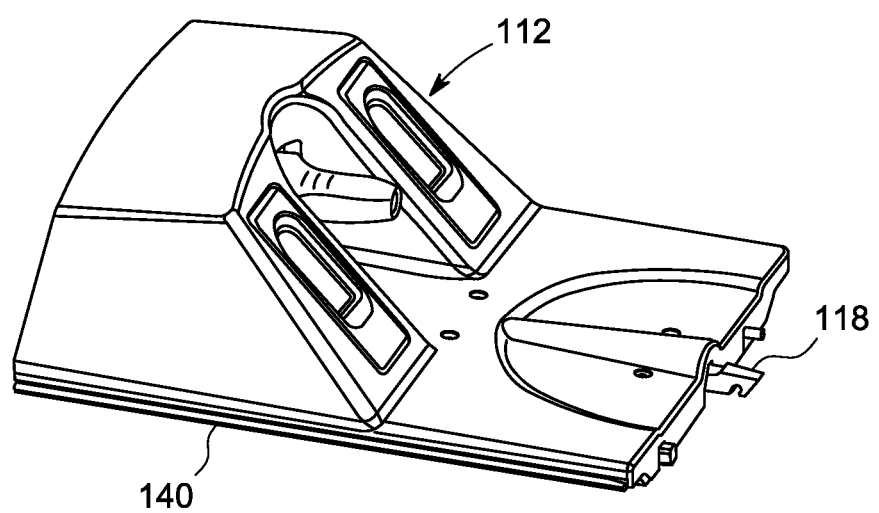
FIG. 5 is a perspective view of a low profile carriage assembly (LPCA) for use in the patient support assembly of FIG. 2 according to an embodiment of the invention.
Figure 6:
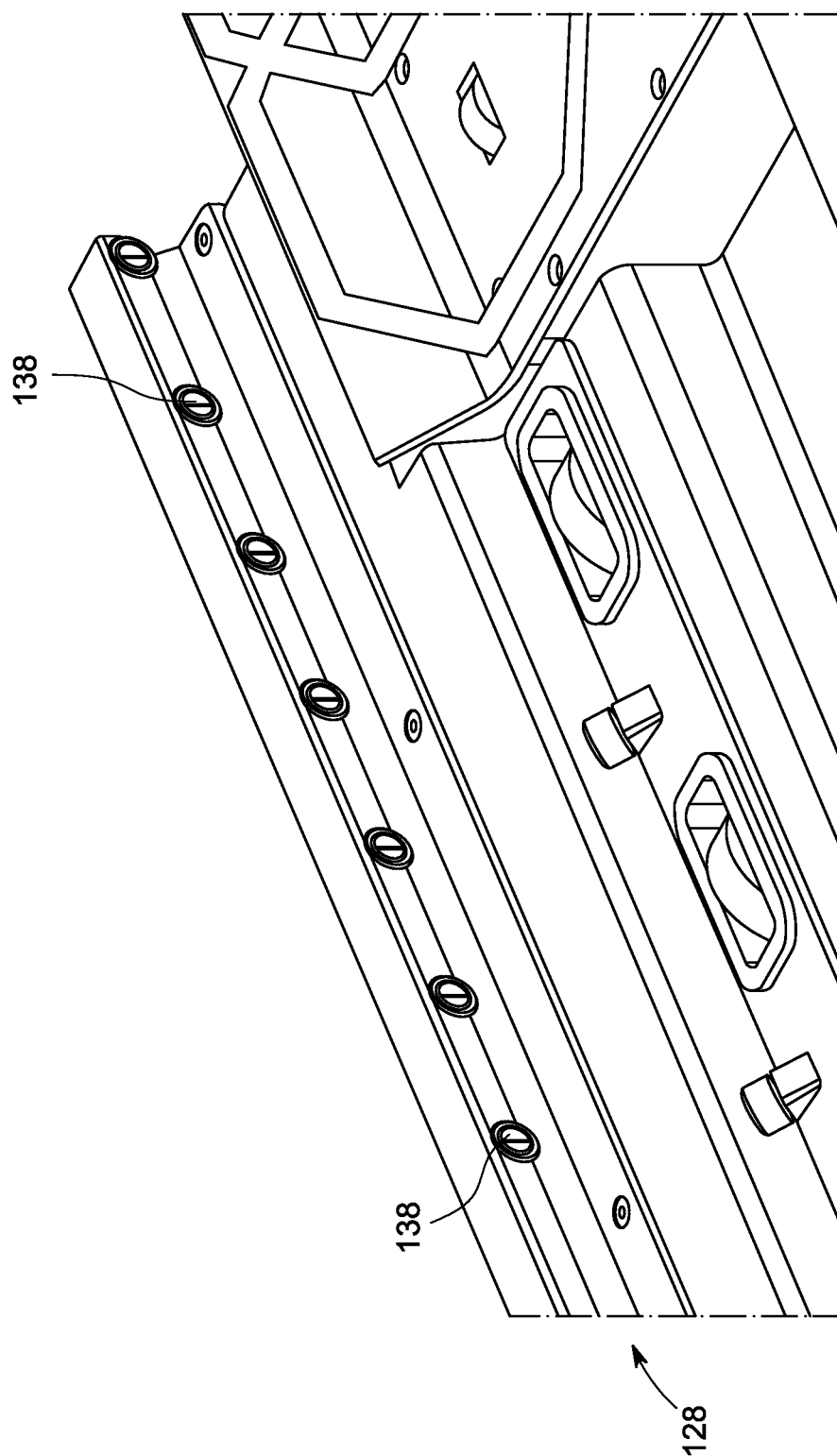
FIG. 6 is a perspective view of a portion of the patient support assembly of FIG. 2 according to an embodiment of the invention.

A more detailed view of the anti-tip rails 128 on the front and rear bridges 94, 96, and of the interaction of the rails 128 with LPCA 112 and cradle 90, is shown in FIGS. 4 and 5. According to an exemplary embodiment, each of rails 128 includes an upper flange 130, a lower section 132 for fastening rail 128 to bridges 94, 96, and a groove 134 that acts as a pinch guard and spill collector throughout the length of the bridge assembly 92 for accommodating spill when interacting with LPCA 112 and cradle 90. The components of the rail thus form a groove 134 that receives the LPCA 112 and cradle 90 therein. According to one embodiment, a set of adjustable ball plungers 136 is provided along an underside of flange 130 on the anti-tip rails 128 in order to control and prevent tipping of the LPCA 112 and/or cradle 90. An alternate embodiment of anti-tip rails 128 on the front and rear bridges 94, 96 is shown in FIG. 6, where the adjustable ball plungers on flanges 130 of the anti-tip rails 128 are replaced by a plurality of rollers or wheels 138 formed on flange 130 of the anti-tip rails 128.

Referring again to FIGS. 4 and 5, each of cradle 90 and LPCA 112 includes slide blades 140 formed on opposing sides thereof that interact with the flanges 130 on anti-tip rails 128. According to one embodiment, the slide blades 140 are formed of a highly lubricate material, such as an ultra-high-molecular-weight polyethylene (UHWM) or similarly suitable material, such that there is a minimal amount of friction between the slide blades 140 and the flanges 130 on anti-tip rails 128. In general, LPCA 112 and cradle 90 roll along roller bearings 120 (FIG. 2) on bridge assembly 92 as they are caused to traverse thereover by dual drive 114 (FIG. 2). However, as the LPCA 112 crosses the gap 106, the LPCA 112 may begin to tip as there are no roller bearings 120 or bridge 92 to support the LPCA 112. Accordingly, as the LPCA 112 traverses gap 106 between the first and second sections 102, 104 of front bridge 94 and is tended toward tipping, the adjustable ball plungers (or rollers) 136/138 on flange 130 attempt to hold the LPCA 112 straight by holding down slide blade 140 on the LPCA 112. The flange 130 and the adjustable ball plungers/rollers 136/138 thereon thus prevent any tipping of the LPCA 112 and provide gap 106 control of the LPCA 112 as it traverses there across.

Figure 7:
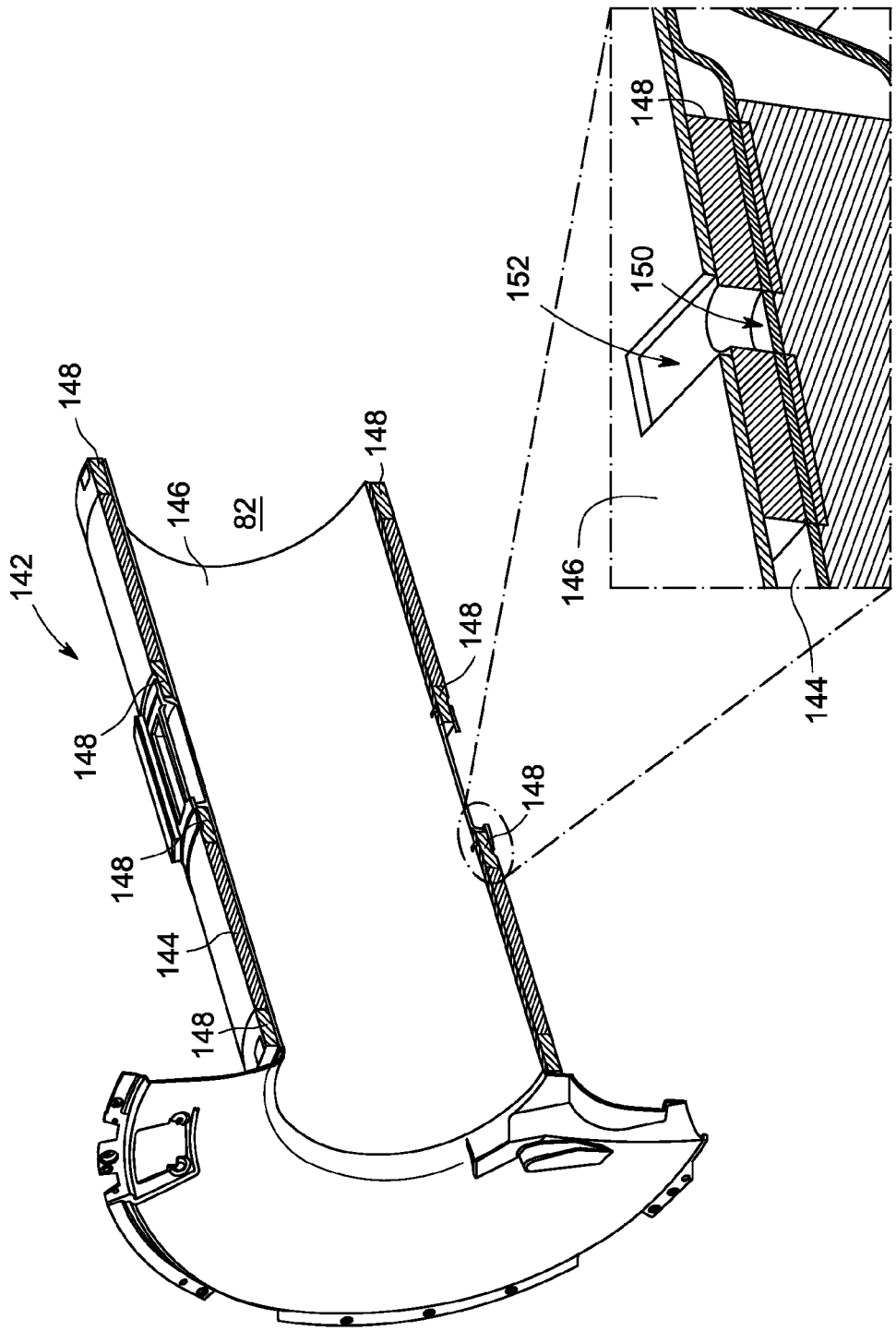
FIG. 7 is a perspective view of a PET tube structure included in the PET-MR imaging system of FIGS. 1 and 3 according to an embodiment of the invention.

Referring now to FIG. 7, a mounting of front bridge 94 to PET-MR imaging system 10 is shown in more detail, according to an embodiment of the invention. A cross-section of a PET tube structure 142 included in PET-MR imaging system 10 is shown in FIG. 7, with the PET tube structure 142 including a PET tube 144 formed about bore 82. A PET tube skin 146 is also included in PET tube structure 142 and is positioned between the PET tube 144 and the patient being imaged. According to an exemplary embodiment, the PET tube structure 142 further includes mounting blocks 148 that are embedded on the PET tube 144 in areas where the first and second sections 102, 104 of front bridge 94 (FIG. 2) are to be secured to the PET tube 144 (i.e., mounting blocks 148 are positioned on each of opposing sides of detector array 70 and adjacent thereto). The mounting blocks 148 are configured to space the PET tube 144 apart from the PET tube skin 146, with the spacing apart of PET tube 144 from PET tube skin 146 providing a thermal barrier therebetween. The separation of PET tube 144 from PET tube skin 146, and the thermal barrier provided thereby, enables a lowering of a temperature of PET tube skin 146 during operation of PET-MR imaging system 10, thereby increasing patient safety and comfort during a scan.

The mounting blocks 148 in PET tube structure 142 provide for anchoring of the first and second sections 102, 104 of front bridge 94 (FIG. 2) to the PET tube 144. According to one embodiment, the mounting blocks 148 each include a threaded hole 150 formed therein, with the PET tube skin 146 having slotted holes 152 therein aligned with the threaded holes 150. The threaded holes 150 on mounting blocks 148 are configured to receive M10 Delrin screws (not shown), for example, with spherical washers (not shown) for mounting the first and second sections 102, 104 of front bridge 94 to PET tube 144. The first and second sections 102, 104 of front bridge 94 can thus be affixed to PET tube 144 via the mounting blocks 148, with no contact being made between the front bridge 94 and the PET tube skin 146 other than this mounting.

Beneficially, embodiments of the invention thus provide a split bridge for use in a PET-MR system that helps in reducing the degradation of PET image quality by minimizing mass in the region of the PET detector array, so as to thereby reduce the attenuation of gamma rays during PET imaging that may result from the presence of such mass. An anti-tip feature is integrated into the split bridge design that provides for LPCA and cradle crossover support of the gap in the split bridge in the area of the PET detector array. The anti-tip feature provides anti-tip support, spill collector and pinch guard functionality. Prevention of CMA load transfer/transmission and lateral guiding of the cradle and LPCA are also accomplished by way of the split bridge design and the design of the cradle and LPCA.

Therefore, according to one embodiment of the invention, a PET-MRI apparatus includes a magnetic resonance imaging (MRI) system having a plurality of gradient coils positioned about a bore of a magnet, and an RF coil assembly coupled to a pulse generator to emit an RF pulse sequence and arranged to receive resulting MR signals from a subject of interest in the bore, along with a positron emission tomography (PET) system having a detector array positioned around a PET tube encircling the bore, with the detector array being controlled to acquire PET emissions of the subject of interest. The PET-MRI apparatus also includes a patient support assembly configured to provide for support and movement of the subject of interest through the bore to enable acquisition of the MR signals and the PET emissions from the subject of interest, with the patient support assembly including a cradle configured to accommodate the subject of interest, a carriage assembly configured to attach to the cradle and cause the cradle to selectively travel through the bore, and a rear bridge configured to receive the cradle and carriage assembly and provide for translation therealong, the rear bridge extending outwardly from a back edge of the PET tube outside a volume of the bore. The patient support assembly also includes a front bridge configured to receive the cradle and carriage assembly and provide for translation therealong, with the front bridge being mounted to the PET tube and further including a first section extending from a front edge of the PET tube into the volume of the bore and a second section extending from the back edge of the PET tube into the volume of the bore, wherein the second section is spaced apart from the first section so as to form a gap in the front bridge between the first section and the second section in an area adjacent the detector array of the PET system, and wherein the rear bridge and front bridge include an anti-tip rail assembly configured to interact with the cradle and the carriage assembly so as to prevent tipping thereof when traversing over the gap between the first and second sections of the front bridge.

According to another embodiment of the invention, a patient support assembly for use in a combination PET-MRI imaging system includes a cradle configured to accommodate a subject of interest, a low profile carriage assembly (LPCA) attachable to the cradle and configured to drive the cradle through an imaging volume of the PET-MRI imaging system, and a bridge assembly configured to accommodate the cradle and LPCA and provide for translation therealong. The bridge assembly includes a rear bridge and a front bridge comprising a first section and a second section, with the front bridge comprising a split bridge that includes a gap formed between the first section and the second section in an area adjacent a PET detector array of the PET-MRI imaging system. The bridge assembly also includes an anti-tip rail assembly configured to interact with the cradle and the LPCA so as to prevent tipping thereof when traversing over the gap between the first and second sections of the front bridge.

According to yet another embodiment of the invention, a PET-MRI apparatus includes a magnetic resonance imaging (MRI) system configured to acquire MR signals from a subject of interest, the MRI system having a plurality of gradient coils positioned about a bore of a magnet and an RF coil assembly coupled to a pulse generator to emit an RF pulse sequence. The PET-MRI apparatus also includes a positron emission tomography (PET) system integrated into the MRI system and having a PET detector positioned on a PET tube encircling the bore, with the PET detector being controlled to acquire PET emissions of the subject of interest. The PET-MRI apparatus further includes a patient support assembly configured to provide for support and movement of the subject of interest through the bore to enable acquisition of the MR signals and the PET emissions from the subject of interest, with the patient support assembly including a low profile carriage assembly (LPCA) configured to drive a patient cradle so as provide for translation of the subject of interest through the bore, with the LPCA including a pair of slide blades formed thereon. The patient support assembly also includes a bridge assembly configured to provide for translation of the LPCA and cradle therealong, with the bridge assembly including a split front bridge having a gap formed therein in an area adjacent the detector array and with the split front bridge further including an anti-tip rail assembly configured to interact with the slide blades on the LPCA to prevent tipping of the LPCA when traversing over the gap in the split front bridge.

This written description uses examples to disclose the invention, including the best mode, and also to enable any person skilled in the art to practice the invention, including making and using any devices or systems and performing any incorporated methods. The patentable scope of the invention is defined by the claims, and may include other examples that occur to those skilled in the art. Such other examples are intended to be within the scope of the claims if they have structural elements that do not differ from the literal language of the claims, or if they include equivalent structural elements with insubstantial differences from the literal languages of the claims.

What is claimed is:

1. A PET-MRI apparatus comprising:
    a magnetic resonance imaging (MRI) system having a plurality of gradient coils positioned about a bore of a magnet, and an RF coil assembly coupled to a pulse generator to emit an RF pulse sequence and arranged to receive resulting MR signals from a subject of interest in the bore;
    a positron emission tomography (PET) system having a detector array positioned around a PET tube encircling the bore, with the detector array being controlled to acquire PET emissions of the subject of interest;
    a coil matrix array (CMA); and
    a patient support assembly configured to provide for support and movement of the subject of interest through the bore to enable acquisition of the MR signals and the PET emissions from the subject of interest, the patient support assembly comprising:
        a cradle configured to accommodate the subject of interest;
        a carriage assembly configured to attach to the cradle and cause the cradle to selectively travel through the bore;
        a rear bridge configured to receive the cradle and carriage assembly and provide for translation therealong, the rear bridge extending outwardly from a back edge of the PET tube outside a volume of the bore;

a front bridge configured to receive the cradle and carriage assembly and provide for translation therealong, the front bridge being mounted to the PET tube and including:

a first section extending from a front edge of the PET tube into the volume of the bore;

a second section extending from the back edge of the PET tube into the volume of the bore, wherein the second section is spaced apart from the first section so as to form a gap in the front bridge between the first section and the second section in an area adjacent the detector array of the PET system; and a coil positioning area configured to house the CMA, the coil positioning area including portions of the first and second sections of the front bridge adjacent one another and including the gap formed between the first section and the second section, with the coil positioning area being a cut-out area of the first and second sections of the front bridge that houses the CMA such that the CMA does not contact the cradle when the cradle traverses over the coil positioning area;

wherein the rear bridge and front bridge include an anti-tip rail assembly configured to interact with the cradle and the carriage assembly so as to prevent tipping thereof when traversing over the gap between the first and second sections of the front bridge.

2. The PET-MRI apparatus of claim 1 wherein each of the rear bridge and the front bridge further comprise a plurality of roller bearings configured to enable translation of the cradle and carriage assembly through the MRI system and PET system in a direction parallel to an axis of the bore.

3. The PET-MRI apparatus of claim 2 wherein a number of the plurality of roller bearings are positioned in the portions of the first and second sections of the front bridge forming the coil positioning area, wherein the number of roller bearings in the coil positioning area are positioned so as to pass through open slots formed in the CMA such that there is no load transfer from the roller bearings to the CMA.

4. The PET-MRI apparatus of claim 1 wherein the front bridge further comprises a set of lateral wheels for lateral positioning of cradle and carriage assembly on the front bridge, in a direction perpendicular to travel of the cradle and carriage assembly along the front bridge.

5. The PET-MRI apparatus of claim 1 wherein the anti-tip rail assembly comprises a pair of anti-tip guide rails positioned on opposing sides of the rear bridge and the front bridge, each of the pair of anti-tip guide rails including an upper flange formed thereon.

6. The PET-MRI apparatus of claim 5 wherein each of the cradle and the carriage assembly further includes slide blades formed thereon configured to interact with the flange on the anti-tip guide rails so as to prevent the cradle and carriage assembly from tipping when traversing over the gap between the first and second sections of the front bridge.

7. The PET-MRI apparatus of claim 5 wherein the each of the anti-tip guide rails comprises adjustable ball plungers or rollers positioned thereon configured to apply a downward pressure onto the slide blades as the carriage assembly traverses over the gap between the first and second sections of the front bridge.

8. The PET-MRI apparatus of claim 1 wherein the PET system comprises a PET tube skin positioned between the PET tube and the subject of interest, and wherein the PET tube skin is spaced apart from the PET tube by a set of mounting blocks embedded on the PET tube, the mounting blocks configured to provide for mounting of the first and second sections of the front bridge to the PET tube.

9. The PET-MRI apparatus of claim 1 wherein the carriage assembly further comprises a dual drive configured to cause the cradle and carriage assembly to move along the front and rear bridges.

10. The PET-MRI apparatus of claim 1 wherein the patient support assembly further comprises a rear pedestal structure configured to support the rear bridge.

11. The PET-MRI apparatus of claim 1 wherein the patient support assembly further comprises a patient table attachable to the front bridge, at the front edge of the PET tube.

12. The PET-MRI apparatus of claim 1 wherein the cradle is composed of a fiber reinforced plastic (FRP) so as to minimize PET attenuation resulting from the cradle; and wherein each of the rear bridge and front bridge comprise a foam core with a skin of FRP.

* * * * *